United States Patent [19]

Curatolo

[11] Patent Number: 5,792,471

[45] Date of Patent: Aug. 11, 1998

[54] DISPENSING DEVICES POWERED BY HYDROGEL

[75] Inventor: William J. Curatolo, Niantic, Conn.

[73] Assignee: Pfizer Inc., New York, N.Y.

[21] Appl. No.: 635,312

[22] Filed: Apr. 19, 1996

Related U.S. Application Data

[62] Division of Ser. No. 960,186, Oct. 9, 1992, Pat. No. 5,516,527, which is a continuation of Ser. No. 655,228, Feb. 12, 1991, abandoned, which is a continuation of Ser. No. 296,464, Jan. 12, 1989, abandoned.

[51] Int. Cl.$^6$ .................................................. A61K 9/36
[52] U.S. Cl. .................. 424/480; 424/464; 424/467; 424/473; 424/489; 424/494
[58] Field of Search ........................ 424/464, 467, 424/473, 480, 489, 494

[56] References Cited

U.S. PATENT DOCUMENTS

| | | | |
|---|---|---|---|
| 4,235,236 | 11/1980 | Theeuwes | 128/260 |
| 4,320,759 | 3/1982 | Theeuwes | 128/260 |
| 4,327,725 | 5/1982 | Cortese et al. | 128/260 |
| 4,578,075 | 3/1986 | Urquhart et al. | 604/892 |
| 4,615,698 | 10/1986 | Guittard et al. | 604/892 |
| 4,723,957 | 2/1988 | Magruder et al. | 424/78 |
| 4,842,867 | 6/1989 | Ayer et al. | 424/473 |

FOREIGN PATENT DOCUMENTS

| | | |
|---|---|---|
| 1238273 | 6/1988 | Canada. |
| 1242394 | 9/1988 | Canada. |
| 0052917 | 6/1982 | European Pat. Off.. |
| 378404 | 7/1990 | European Pat. Off.. |

*Primary Examiner*—Jyothsan Venkat
*Attorney, Agent, or Firm*—Peter C. Richardson; Gregg C. Benson; A. Dean Olson

[57] ABSTRACT

This invention relates to devices useful for the controlled delivery of one or more beneficial agents to an environment of use. More specifically, this invention concerns such devices which are powered by hydrogel. This invention also relates to the controlled delivery of one or more beneficial agents to an aqueous environment of use through the use of such hydrogel powered dispensing devices. Also disclosed are methods for the controlled delivery of one or more beneficial agents to an aqueous environment of use which comprises administering to or otherwise placing the devices of this invention in the environment of use.

17 Claims, 3 Drawing Sheets

DISPENSING DEVICES POWERED BY HYDROGEL

This is a division of application Ser. No. 07/960,186 filed on Oct. 9, 1992, now U.S. Pat. No. 5,516,527, which was a continuation of Ser. No. 07/655,228 filed on Feb. 12, 1991, now abandoned, which was a continuation of application Ser. No. 07/296,464 filed on Jan. 12, 1989, now abandoned.

BACKGROUND OF THE INVENTION

1. Field of the Invention

This invention relates to devices useful for the controlled delivery of one or more beneficial agents to an environment of use. More specifically, this invention concerns such devices which are powered by hydrogel. This invention also relates to the controlled delivery of one or more beneficial agents to an aqueous environment of use through the use of such hydrogel powered dispensing devices. Further, still, this invention is concerned with devices for the controlled delivery of one or more beneficial agents to the physiological fluid of animals including mammals such as human beings.

2. General Background of the Invention

The desirability of controlled release of beneficial agents into an environment of use such as the physiological fluid of animals including mammals such as human beings is well known to those skilled in the relevant art. Controlled delivery of beneficial agents such as drugs can, for example, result in a relatively constant concentration of such agents in the physiological fluids of an animal instead of the more dramatic rises and subsequent decreases in concentration of such agents usually associated with periodic dosing. Furthermore, controlled delivery of drugs can eliminate certain deleterious effects sometimes associated with a sudden, substantial rise in the concentration of certain drugs.

A variety of devices for the controlled delivery of beneficial agents have been described. Certain of those devices employ the physical phenomenon of diffusion for their operation. Examples of such diffusion driven devices are disclosed in U.S. Pat. No. 4,217,898. Other devices have been described which operate with the principle of colloidal osmotic pressure. Examples of such osmotically driven devices are disclosed in U.S. Pat. Nos. 3,845,770; 3,995,631; 4,111,202; 4,160,020; 4,439,196 and 4,615,698. Devices which employ a swellable hydrophilic polymer which polymer exerts pressure on a container and thereby forces drug therefrom is disclosed in U.S. Pat. No. 4,180,073. U.S. Pat. No. 4,327,725 discloses a device which employs a layer of fluid swellable hydrogel to force beneficial agent out of the device through a specified and defined passageway. Other hydrogel powered devices containing such a passageway for delivery of beneficial agents are disclosed in GB 2,140,687A.

Applicant's copending application, assigned to the assignee hereof and filed concurrently herewith entitled "Dispensing Devices Powered by Lyotropic Liquid Crystals" bearing applicant's docket number PC7540/GCB, discloses dispensing devices, powered by lyotropic liquid crystals, for the controlled delivery of one or more beneficial agents to an environment of use.

It is an object of this invention to provide devices for the controlled delivery of one or more beneficial agents to an environment of use. Another object of this invention is to provide devices powered by hydrogel which will effect the controlled delivery of one or more beneficial agents to an aqueous environment of use. Yet another object of this invention is to provide devices powered by hydrogel for the controlled delivery of one or more beneficial agents to the physiological fluids of an animal including a human being. This invention also has as an object the provision of a device to controllably deliver one or more beneficial agents which are insoluble or substantially insoluble in water or physiological fluids. Another object still of this invention is to provide devices powered by hydrogel which do not require a specified and defined passageway to operate but, instead, comprise a plurality of pores. It is another object of this invention to provide devices powered by hydrogel which do not require a semi-permeable coating, but, instead, can employ a coating which is permeable to the beneficial agent. Further still, it is an object of this invention to provide devices powered by hydrogel which can assume a variety of shapes and sizes and devices which can be delivered to an environment of use in a capsule.

It is also an object of this invention to provide methods for the controlled delivery of one or more beneficial agents to an environment of use by administering to or otherwise placing the device of this invention into the environment.

These and other objects of this invention will be readily apparent to those skilled in the relevant art enabled by the disclosure herein.

SUMMARY OF THE INVENTION

This invention concerns devices for the controlled delivery of one or more beneficial agents to an environment of use which devices comprise a mixture of one or more beneficial agents and hydrogel surrounded by a coating of a material that is permeable to water and/or aqueous medium such as physiological fluid and which coating contains one or more holes and/or a plurality of pores. The pores in the coating can be formed by mechanical/physical means or result from dissolution of a porosigen in the coating upon placing the devices in an aqueous environment of use.

This invention also concerns devices for the controlled delivery of one or more beneficial agents to an aqueous environment of use which devices comprise two adjacent layers, the first layer comprising a mixture of one or more beneficial agents and hydrogel and the second layer comprising hydrogel of the same or different composition as the hydrogel in the first layer. Such devices have a coating comprising a material which is permeable to water and/or aqueous medium and which contains one or more holes and/or a plurality of pores such as the devices described above.

All of the devices of this invention optionally can include therein one or more excipients and/or osmotically effective solutes.

This invention also relates to capsules which contain one or more of the devices as described above.

Further, this invention concerns methods for the controlled delivery of one or more beneficial agents to an aqueous environment of use which comprise administering to or otherwise placing the devices and/or the capsules of this invention in the environment of use.

DETAILED DESCRIPTION OF THE DRAWINGS

FIGS. 1–6 depict certain embodiments of the devices of this invention and are meant to be illustrative of such embodiments of the invention herein. The Figures are not to be construed as limiting in any way the scope of this invention to the embodiments depicted therein. Further, the various components of the devices depicted in the Figures are representational and are not necessarily drawn to scale.

Figure 1:
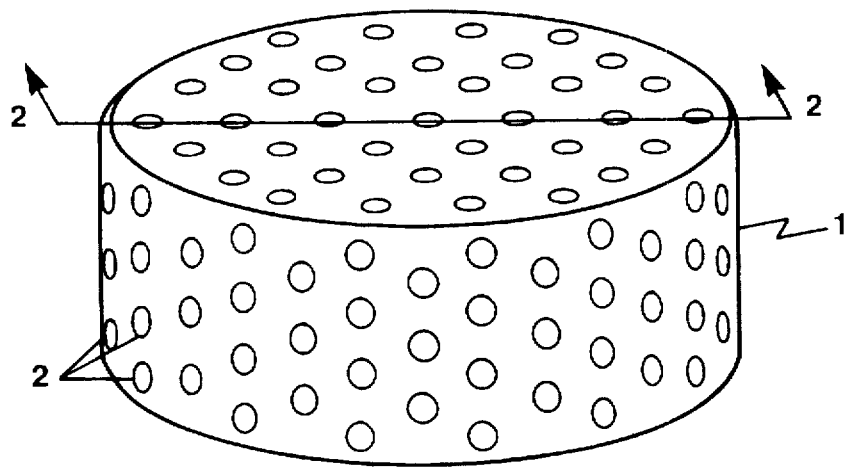
FIG. 1 is a perspective view of one embodiment of the device (1) of this invention in the shape of a tablet.

FIG. 1 shows one embodiment of the device (1) of this invention in the form of a tablet containing a plurality of pores (2).

Figure 2:
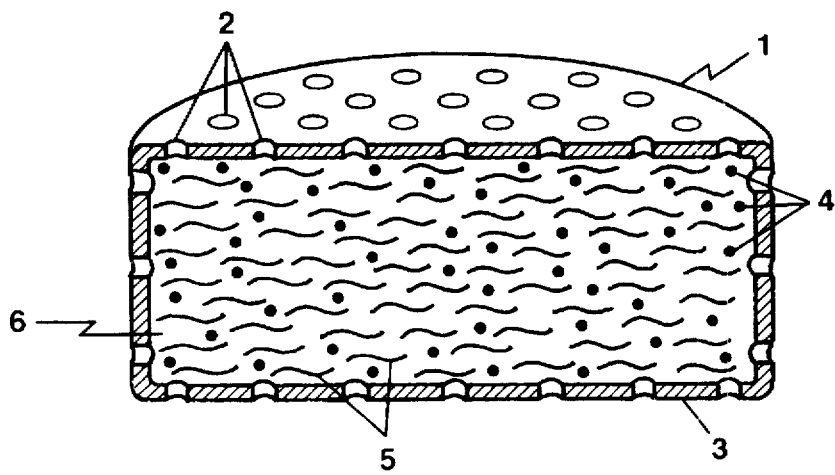
FIG. 2 is a cross-sectional view taken along line 2—2 of the device (1) shown in FIG. 1.

FIG. 2 is a cross-sectional view taken along line 2—2 of FIG. 1 and shows the coating (3) of the device (1) which contains a plurality of pores (2) in and through the coating (3). A mixture (6) of one or more beneficial agents represented by dots (4) and hydrogel represented by wavy lines (5) is contained within the surrounding coating (3).

Figure 3:
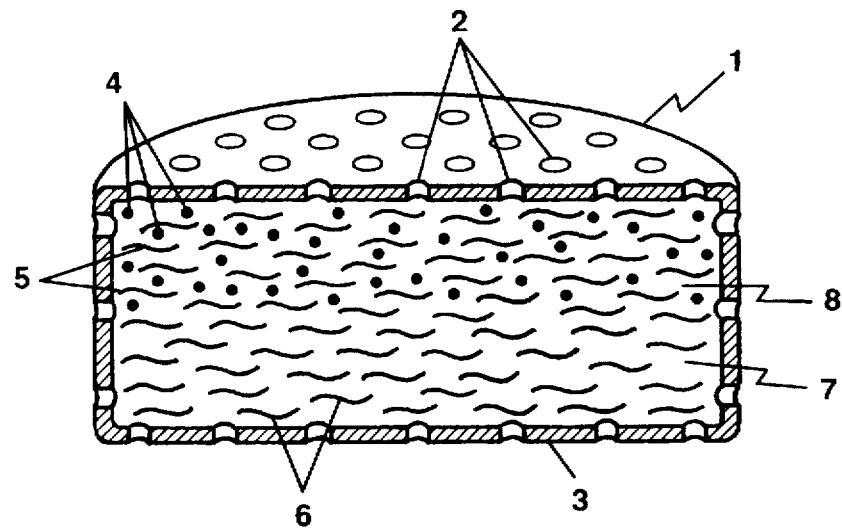
FIG. 3 is a cross-sectional view of another embodiment of the device (1) which is taken along line 2—2 of the device (1) shown in FIG. 1 which device comprises two layers (6 and 7) within the surrounding coating (3) of the device (1).

FIG. 3 is a cross-sectional view of another embodiment of the device (1) shown in FIG. 1 wherein the device (1) comprises two layers (6 and 7) within the surrounding coating (3). FIG. 3 is a cross-sectional view taken along line 2—2 of FIG. 1 and shows the coating (3) of the device (1) which contains a plurality of pores (2) in and through the coating (3). Contained within the surrounding coating (3) are a first layer (6) which comprises a mixture of one or more beneficial agents represented by dots (4) and hydrogel represented by wavy lines (5) and a second layer (7) which comprises hydrogel represented by wavy lines (8) which can be the same or different than hydrogel (5). Layer (7) is adjacent to layer (6) and comprises an area in contact therewith.

Figure 4:
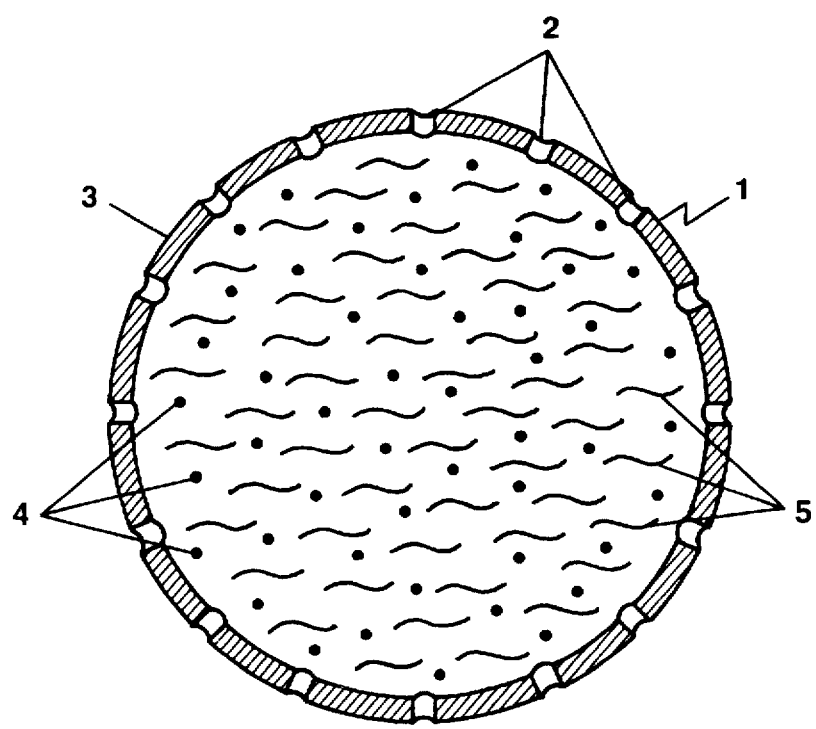
FIG. 4 is a cross-sectional view through the axis of another embodiment of the device (1) of this invention wherein the device (1) is a sphere or is substantially spherical in shape.

FIG. 4 is a cross-sectional view through the axis of another embodiment of the device (1) of this invention wherein the device is a sphere or is substantially spherical in shape. The device (1) contains a plurality of pores (2) in and through the coating (3). Within the surrounding coating (3) is a mixture (6) of one or more beneficial agents represented by dots (4) and hydrogel represented by wavy lines (5).

Figure 5:
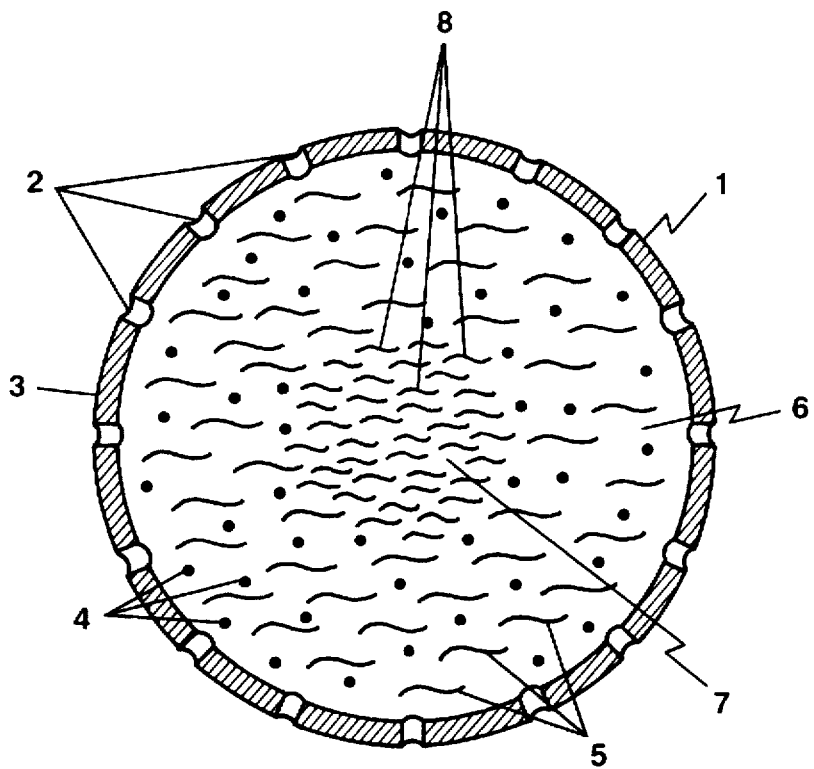
FIG. 5 is a cross-sectional view through the axis of another embodiment of the device (1) of this invention wherein the device (1) is a sphere or is substantially spherical in shape and which comprises two-layers (6 and 7) within the surrounding coating (3) of the device (1).

FIG. 5 is a cross-sectional view through the axis of another embodiment of the device (1) of this invention wherein the device (1) is a sphere or is substantially spherical in shape. The device (1) contains a plurality of pores (2) in and through the coating (3). Within the surrounding coating (3) are two layers (6 and 7). The outermost layer (6) comprises a mixture of one or more beneficial agents represented by dots (4) and hydrogel represented by wavy lines (5) and the innermost layer (7) comprises hydrogel represented by wavy lines (8) which can be the same or different than hydrogel (5).

Figure 6:
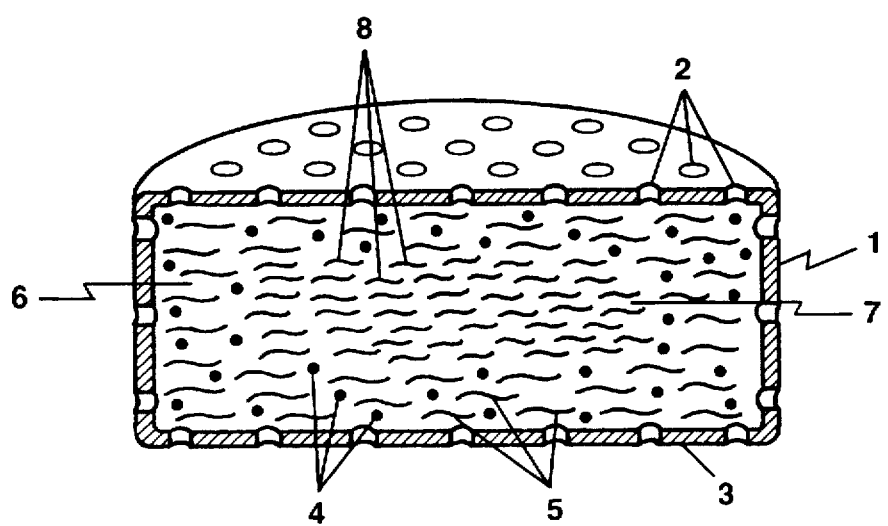
FIG. 6 is a cross-sectional view of another embodiment of the device (1) which is taken along line 2—2 of the device (1) shown in FIG. 1 which comprises two layers (6 and 7) within the surrounding coating (3) of the device (1).

FIG. 6 is a cross-sectional view of another embodiment of the device (1) shown in FIG. 1 which view is taken along line 2—2 of FIG. 1 and which device (1) comprises two layers (6 and 7) within the surrounding coating (3). The coating (3) contains a plurality of pores (2) in and through the coating (3). Contained within the surrounding coating (3) are an outermost layer (6) which comprises a mixture of one or more beneficial agents represented by dots (4) and hydrogel represented by wavy lines (5) and an innermost layer (7) which comprises hydrogel represented by wavy lines (8) which can be the same or different than hydrogel (5).

DETAILED DESCRIPTION OF THE INVENTION

This invention relates to devices powered by hydrogel for the controlled delivery of one or more beneficial agents to an environment of use.

The hydrogels employed in the various embodiments of the devices of this invention are well known to those skilled in the relevant art. For example, U.S. Pat. No. 4,327,725 describes various hydrogels and the teachings thereof concerning such hydrogels are hereby incorporated herein by reference. The term hydrogel, as used herein, shall be construed to mean a water swellable polymer or a combination of two or more such polymers. Such hydrogels, for the purpose of this invention, comprise polymeric materials which, when in contact with water or other aqueous medium, will absorb such water/medium and swell to a certain extent. Such absorption can be reversible or irreversible and still be within the scope of this invention. A preferred hydrogel for use in the devices of this invention is polyethylene oxide (PEO). PEO is commercially available and can be obtained having a variety of different molecular weights. For example, PEO can be obtained with molecular weights of 8K, 14K, 100K, 400K, 600K, 1,000K or 5,000K. The particular molecular weight of PEO or other hydrogels employed in the devices of this invention will vary as a function of the pore size in the coating and the release rate which is to be achieved for the particular beneficial agent or agents to be delivered.

In the two layer embodiments of the devices of this invention, such as those shown in FIGS. 3, 5 and 6, the hydrogel of each layer may be the same or may be different. In the embodiment depicted in FIG. 3, it is preferred that the hydrogel (8) of layer (7) be of a higher molecular weight than hydrogel (5) of layer (6). Still more preferably, the hydrogel (8) of such an embodiment as shown in FIG. 3 should be of a sufficiently high molecular weight that substantially no hydrogel is capable of leaving the device (1) through the pores (2). However, since certain hydrogels such as PEO increase in viscosity as a function of increase in molecular weight, the hydrogel (5) and (8) must be chosen or blended such that it provides sufficient swelling properties but does not cause the device to burst. Selection of the appropriate hydrogel (5) and (8) for such devices is within the skill of those who practice in the relevant art enabled by the disclosure herein.

The hydrogel employed in the various embodiments of the devices of this invention can be a blend of, for example, two or more polymers. By way of example and not of limitation, different hydrogels comprising blends of PEO polymers of different molecular weights can be prepared and employed in the devices of this invention and are deemed within the scope hereof. Such blends can, for particular beneficial agents, be adjusted to assist in achieving the desired delivery rates for the agents.

In addition to the hydrogel(s), the devices of this invention may also contain an osmotically effective solute for the purpose of providing a colloidal osmotic pressure which is additive with the swelling pressure of the hydrogel(s). Examples of osmotically effective solutes are inorganic and organic salts, and sugars. A preferred composition comprising such a solute contains a range of 0–30% osmotically effective solute. Of course, for the devices of this invention which are to be employed to deliver a drug to an animal, any such solute must be pharmaceutically acceptable.

The devices of this invention comprise, in addition to the hydrogel and the optional osmotically effective solute described above, one or more beneficial agents. The term beneficial agents as used in this specification and the accompanying claims includes, by way of example and not of limitation, any physiologically or pharmacologically active substance that produces a localized or systemic effect in animals. The term animals is meant to include mammals including human beings as well as other animals. The physiologically or pharmacologically active substance of this invention need not be soluble in water. Indeed, an advantage of the devices of this invention is that such insoluble or partially insoluble substances as well as soluble substances can be delivered to the environment of use in a controlled fashion by the devices hereof.

Examples of active substances employed in the devices of this invention include, without limitation, inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. The drug that can be delivered for acting on these systems includes anti-depressants, hypnotics, sedatives, psychic energizers, tranquilizers, anti-convulsants, muscle relaxants, antisecretories, anti-parkinson agents, analgesics, anti-inflammatory agents, local anesthetics, muscle contractants, antibiotics, anti-microbials, anthelmintics, anti-malarials, hormonal agents, contraceptives, histamines, antihistamines, adrenergic agents, diuretics, antiscabiosis, anti-pediculars, anti-parasitics, anti-neoplastic agents, hypoglycemics, electrolytes, vitamins, diagnostic agents and cardiovascular drugs. Also included in such active substances are prodrugs of the above-described drugs. Such drugs or prodrugs can be in a variety of forms such as the pharmaceutically acceptable salts thereof. However, a particular advantage of the devices of this invention is that such beneficial agents, such as the drugs and prodrugs described above, need not be soluble in water in order for the devices of this invention to deliver, in a controlled manner, such agents. It is within the scope of this invention that the devices can contain more than one beneficial agent.

Devices of this invention are particularly advantageous for delivering two or more drugs simultaneously. The rate of drug release is controlled primarily by the extrusion rate of hydrogel and is relatively independent of the solubility of the incorporated drugs. Thus two or more incorporated drugs will be released at absolute rates which depend upon their individual loadings in the device. For example, devices of the current invention can be used to co-deliver a sustained dose of an α-blocker, such as prazosin, and a diuretic, such as polythiazide, for the treatment of hypertension. For the treatment of cold symptoms, devices of this invention can be used to deliver a combination of a decongestant, such as pseudephedrine hydrochloride, and an antihistamine, such as chlorpheniramine maleate. For treatment of cough/cold symptoms, three or more drugs can be released in a controlled fashion from a device of this invention; for example a combination of an analgesic, a decongestant, an antihistamine, and an antitussive can be delivered. A person skilled in the art will recognize that the current invention can be used to provide controlled and sustained delivery of a wide variety of combinations of drugs.

The beneficial agent of this invention also includes other substances for which it is desirable and/or advantageous to control delivery into an environment of use. Examples of such substances include, but are not limited to, fertilizers, algacides, reaction catalysts and enzymes.

The devices of this invention also comprise a coating (3) which surrounds the mixture (6) of one or more beneficial agents (4) and hydrogel (5) or, in the two layer embodiments hereof, which surrounds both layers (6 and 7) except for the area in contact between such layers. The coating (3) comprises at least one water permeable polymer but, significantly and in contrast to many prior art devices, the coating need not be semi-permeable. Therefore, the coating (3) can be freely permeable to low molecular weight compounds. By way of example and not of limitation, such polymers for the coating (3) include cellulose acetate, ethyl-cellulose, silicone rubber, cellulose nitrate, polyvinyl alcohols, cellulose acetate butyrate, cellulose succinate, cellulose laurate, cellulose palmitate and the like. For example, suitable coatings are obtained with cellulose acetate having an average molecular weight of 40K or 60K. Also suitable for the coating (3) of the devices of this invention are biodegradable polymers which do not degrade significantly (i.e., break or burst) during the delivery period. Examples of such biodegradable polymers include polylactic acid, polyglycolic acid and poly(lactide-coglycolide). A preferred polymer for the coating (3) is cellulose acetate.

The coating (3) can also comprise one or more porosigens such that, when the devices of this invention are placed in an environment of use, said porosigen(s) dissolve and effect the formation of a plurality of pores (2) in and through the coating (3).

As stated above, the porosigens can be employed alone or in combination to effect formation of the pores (2) in and through the coating (3). The ratio of porosigen or porosigens to coating polymer can be varied as well as the choice of porosigens to be employed. Such variations are within the skill of those who practice in the art and will be determined by such factors as the solubility of the beneficial agent(s), the particle size of the agent(s), the molecular weight of the hydrogel and the desired rate of release. Examples of porosigens which will function to form the pores (2) in and through the coating (3) include inorganic salts such as sodium chloride, potassium chloride, potassium phosphate and the like. Other effective porosigens are certain particulate organic compounds and salts thereof such as glucose, sucrose, lactose, succinic acid, sodium succinate, sodium carbonate and the like. Also effective porosigens are water-soluble polymers such as polyethyleneglycol (PEG), methyl cellulose, hydroxy-propylmethyl cellulose, hydroxypropyl cellulose (HPC), polyethylene oxide (PEO) and the like. Such pore-forming polymers must, however, have the ability to form a phase-separated coating when mixed with the coating forming polymer of this invention. That is to say, the porosigen polymer and the coating polymer cannot be totally miscible. Combinations of porosigens such as particulate organic compounds and salts thereof with inorganic salts and/or water-soluble polymers can be employed and are within the scope of this invention. Similarly, inorganic salts with water-soluble polymers can be employed as porosigens in the devices of this invention. When the devices of this invention are to be used to deliver beneficial agents to an animal, the porosigen or porosigens employed must be pharmaceutically acceptable.

In addition to the formation of pores (2) upon placement of the devices of this invention into an environment of use through dissolution of one or more porosigens, the pores (2) can be preformed. Such preformed pores can be produced by methods well known to those skilled in the art such as by gas generation in the coating (3) during formation of the coating (3); etched nuclear tracking; laser, sonic or mechanical drilling; or electric discharge. It is preferred, however, that such pores result from dissolution of porosigen(s) as described above.

In addition to the pores described above, or instead thereof, the coating can contain one or more holes. The holes may extend through only the coating on one face of the device or extend through the entire device. However, it is preferred that for the two layer embodiments of the devices of this invention of the type represented in FIG. 3 wherein, in addition to the pores shown or instead thereof, one or more holes are contained in the coating, such holes do not extend through the entire device but only extend through the coating adjacent to the layer comprising beneficial agent. Such holes are made by standard methods known to those skilled in the art such as by mechanical, sonic or laser drilling.

In addition to the above-mentioned components of the devices of this invention, other common pharmaceutical excipients may be present. Examples of such excipients include, but are not limited to, binders such as microcrystalline cellulose, plasticizers such as polyethyleneglycol-600, and buffers such as sodium phosphate.

The devices of this invention can be prepared in a variety of sizes and shapes. The particular size and shape of the device will be determined, in part, by the particular use to which the device is to be put. For example, for oral administration of a drug, the device of this invention can be in the shape of a tablet or caplet, is of suitable size for containing the desired dosage of drug and is capable of oral administration. Other shapes of the devices of this invention include, by way of example and not of limitation, cylindrical or conical shapes suitable for administration of drugs intravaginally and/or rectally and convex shaped devices for ocular administration of drugs.

The devices of this invention can also be administered within a capsule comprising a water soluble wall. For example, the devices of this invention can be manufactured to be of suitable size for inclusion either singly or multiply within a gelatin capsule such that when the capsule dissolves the device or devices are released into the environment of use. While the devices to be included within a capsule can be of a variety of shapes, a preferred embodiment for such devices is spherical or substantially spherical. The exact number and size of such devices can and will be determined according to a variety of factors well known to those skilled in the art. For example, the environment of use, the beneficial agent or agents, the amount of beneficial agent and the rate of release are all factors to be considered in determining the size, shape and number of devices to be included in such capsules as well as the composition of the capsule.

While the actual process used to manufacture the devices of this invention may vary, one such preferred process is described below. Polymer to serve as the hydrogel (5) is blended according to standard methods well known to those skilled in the art in a predetermined ratio (e.g. weight percent) with one or more beneficial agents (4) and any excipients and/or osmotically effective solute(s). The ratio used will vary to a greater or lesser degree depending upon the particular hydrogel, the particular beneficial agent(s) used and the release rate to be achieved. Generally, however, the devices of this invention will comprise hydrogel in an amount from about 50 to about 95 weight percent based on the total weight of the mixture (6) of hydrogel (5) and beneficial agent(s) (4), and any excipients and/or osmotically effective solute(s). The hydrogel (5) can comprise more than one polymer in which case all polymers are blended with the beneficial agent(s) (4) and any excipients and/or osmotically effective solute(s) either sequentially or simultaneously, optionally and preferably, the polymer(s) is sieved to a desired mesh cut prior to blending. If the desired device is to comprise one layer of the blended mixture (6) such as is shown in FIG. 2, then the resulting blended mixture (6) is pressed into the desired shape such as a tablet or caplet using a conventional tableting press such as a Kilian LX-21 rotary tablet press (Kilian and Co., Koln, Germany).

Devices (1) of this invention which comprise two layers (6 and 7), such as those of the type shown in FIG. 3, can be prepared in a similar but modified manner using a conventional bilayer tablet press. One layer consists of a mixture of one or more hydrogel polymers with one or more beneficial agents. The other layer consists of one or more hydrogel polymers, preferably of higher viscosity than, and generally of higher molecular weight than, the hydrogel polymer(s) which are mixed with the beneficial agent(s) in the first layer.

Spherical or substantially spherical embodiments such as depicted in FIGS. 4 and 5 can be prepared in a variety of ways known to those skilled in the art. In a preferred method, such embodiments are prepared using a Fuji extruder/spheronizer (Fuji Paudal Co., Tokyo, Japan) according to methods well known to those skilled in the art. When concentrically arranged embodiments are desired, hydrogel core beads are first prepared. These hydrogel beads then can be coated with a hydrogel/drug mixture using a Freund CF-granulator (CF-360; Freund Industrial Co., Tokyo, Japan) or a Glatt GPCG coating apparatus (Glatt Air Techniques, Ramsey, N.J.).

Following formation of the desired shape in the press or extruder/spheronizer, coating (3) is applied to the entire surface of the mixture (6), or the surface of layers (6) and (7) which are not in contact with each other, or the outer surface of the outermost layer (6) of the concentric embodiment such as depicted in FIG. 5. The coating (3), which also can comprise porosigen(s), is applied to the mixture or outermost layer (6) or layers (6) and (7) according to standard methods well known to those skilled in the art. For those devices which are not spherical or substantially spherical, it is preferred that such coating be applied by spraying using, for example, a Freund Model HCT-30 Hicoater (Freund Industrial Co., Tokyo, Japan). For those devices which are spherical or substantially spherical, it is preferred that such coating be applied using, for example, a Freund CF-granulator or a Glatt GPCG coating apparatus as described above. As an example, when cellulose acetate is employed for the coating, it can be sprayed as an acetone solution (5%) or as other solutions such as in acetone/methanol (9:1). Such cellulose acetate coatings from acetone/methanol solution result in a more opaque coating but have little or no observable impact on the functioning of the devices of this invention. The amount of coating (3) to be applied can be varied to affect the release rate of the devices but will generally be from about 4 to 50 weight percent of the total device weight with a range of from about 6 to 50 weight percent for those coatings (3) comprising porosigen(s).

For devices (1) of this invention which contain coating (3) in which the plurality of pores (2) is formed by means other than dissolution of porosigen(s), a preferred amount of coating (3) is in the range of from about 6 to 25 weight percent with an even more preferred range being from about 8 to 20 weight percent. If such coating (3) contains porosigen(s), then a preferred amount of coating (3) for the devices (1) of this invention is a range of from about 8 to 30 weight percent with an even more preferred range being from about 10 to 25 weight percent.

If the coating (3) contains one or more porosigens, then the pores (2) will be formed in situ when the device (1) is placed in the environment of use. Of course, while not necessarily advantageous, the pores (2) of such devices can be preformed by placing the device first into a suitable aqueous environment then, upon dissolution or partial dissolution of the porosigen(s), into the environment of use.

If the coating (3) does not contain any porosigen, then the pores (2) can be formed by other methods well known to those skilled in the art. For example, pores (2) in coating (3) can be formed by gas generation during formation of the coating (3) following application of the coating mixture to the device. Other processes to produce pores (2) in coating (3) include the use of etched nuclear tracking, the use of laser, sonic or mechanical drilling and the use of electrical discharge. Additionally, in coatings without porosigens, pores can be formed in the environment of use by bursting of weak portions of the membrane as a result of the internal pressure generated by the swelling hydrogel.

A combination of the above described methods for producing pores (2) in coating (3) can be employed and are within the skill of those skilled in the art enabled by the disclosure herein. Such devices are within the scope of this invention.

When employing porosigens to form the pores (2) in coating (3), particular attention is to be paid to the beneficial agent or agents to be delivered by the device (1). If the beneficial agent is soluble, then pore size is not as crucial as when the agent is insoluble. Indeed, the devices of this invention will function to controllably release certain agents even though the pore size is less than 0.1 micron where such agent is soluble. However, where delivery of an insoluble agent, such as the drug glipizide, is desired, then the porosigen employed must be such that, upon dissolution, pores (2) having diameters greater than the particle size of the agent are formed in and through the coating (3). For example, sucrose of a selected mesh cut can be employed in a suspension comprising cellulose acetate to form a coating (3) which, upon subsequent dissolution of the sucrose will yield pores (2) of a preselected (i.e., mesh cut) size. Similarly, commercially available sucrose beads can be so employed. For certain beneficial agents and/or environments of use, it may be advantageous or preferable to include more than one porosigen. For example, coating mixtures which comprise coating polymer, water soluble polymer and sucrose such as cellulose acetate/polyethylene glycol-600 (1:1) with 50% particulate sucrose can be suitably employed. The choice of porosigen or porosigens as well as the amount thereof employed in the coating mixture can be readily determined by those skilled in the art enabled by this disclosure.

Similarly, when the pores (2) in coating (3) are formed by means other than by dissolution of porosigen(s), the nature of the beneficial agent(s) to be delivered by the device (1) must be considered to insure that the pores (2) are of a sufficient diameter as described above. Formation of pores (2) of varying diameter according to the methods described above are well known to those skilled in the art.

When the devices of this invention are to contain one or more holes in the coating (3) or through the device (1), then, after such devices have been coated as described above, the desired number and size holes are drilled through the coating or device according to standard methods such as mechanical, sonic or laser drilling.

Methods for using the devices of this invention include administration of the appropriate devices to animals via oral administration or by insertion of the appropriate devices into a body cavity of the animal. Devices of this invention can also be used to deliver agents to such environments of use as fish tanks, soil and aqueous chemical and/or enzymatic reaction systems. In such cases, the devices are placed into the desired environment of use. The devices of this invention require that any such environment of use be either aqueous or provide for contact of the device with water or other aqueous medium.

The following examples will serve to illustrate the devices of this invention and are not to be construed as limiting the scope hereof to those embodiments specifically exemplified.

EXAMPLE 1

Doxazosin mesylate was blended with 20K molecular weight polyethylene oxide (PEO-20K) in a ratio of 2:98 and the blended mixture was pressed into 500 mg tablets in a Carver press using 13/32 inch standard concave punches under 2 metric tons for 2 seconds. The tablets were then spray coated with a 9:1 acetone/methanol solution of cellulose acetate (2.2%) and hydroxypropyl-cellulose (HPC) (2.2%). The weight ratio of cellulose acetate to HPC in the coating was 1:1, and the final coating was 12 weight percent of the total device weight.

EXAMPLE 2

The procedure of Example 1 was followed up to the coating of the tablets where the coating mixture was applied to an amount equal to 18.6 weight percent of the total device weight.

EXAMPLE 3

The procedure of Example 1 was followed up to the coating of the tablets where the coating mixture was applied to an amount equal to 23.8 weight percent of the total device weight.

EXAMPLE 4

Tablets of 500 mg were prepared as follows. Polyethylene oxide (14K molecular weight) (PEO-14K) was blended with doxazosin mesylate at a ratio of 9:1 and pressed into 500 mg tablets as described in Example 1. Then, the tablets were spray coated with a 9:1 acetone/methanol solution of cellulose acetate (2.2%) and HPC (2.2%). The weight ratio of cellulose acetate to HPC in the coat was 1:1, and the final coating was 13.1 weight percent of the total device weight.

EXAMPLE 5

The procedure of Example 4 was followed to form tablets which were then spray coated with an 8:2 acetone/methanol solution of cellulose acetate (2.9%) and HPC (4.3%). The weight ratio of cellulose acetate to HPC in the coating was 2:3, and the final coating was 14 weight percent of the total device weight.

EXAMPLE 6

The procedure of Example 4 was followed to form tablets which were then spray coated with an 8:2 acetone/methanol solution of cellulose acetate (1.5%) and HPC (3.5%). The weight ratio of cellulose acetate to HPC in the coating was 3:7, and the final coating was 13.1 weight percent of the total device weight.

EXAMPLE 7

A blend of PEO of 8K molecular weight (PEO-8K) and doxazosin mesylate (98:2) was prepared and pressed into 500 mg tablets in a Carver press using 13/32 inch standard concave punches under 2 metric tons for 2 seconds. The tablets were then spray coated with a 9:1 acetone/methanol solution of cellulose acetate (3%) and PEO-8K (3%). The weight ratio of cellulose acetate to PEO-8K in the coating was 1:1, and the final coating was 12.7 weight percent of the total device weight.

EXAMPLE 8

A blend of polyethylene oxide (8K molecular weight) (PEO-8K) and doxazosin mesylate (9:1) was prepared and pressed into 500 mg tablets in a Carver press using 13/32 inch standard concave punches under 2 metric tons for 2 seconds. The tablets were spray coated with a 9:1 acetone/methanol solution of cellulose acetate (3.5%) and polyethylene glycol (molecular weight 600) (PEG-600) (1.5%). The weight ratio of cellulose acetate to PEG-600 in the coating was 7:3, and the final coating was 12.5 weight percent of the total device weight.

EXAMPLE 9

The procedure of Example 8 was followed to produce tablets which were then spray coated with a 9:1 acetone/methanol solution of cellulose acetate (3.0%) and PEG-600 (2.0%). The weight ratio of cellulose acetate to PEG-600 in the coating was 3:2, and the final coating was 12.9 weight percent of the total device weight.

EXAMPLE 10

The procedure of Example 8 was followed to produce tablets which were then spray coated with a 9:1 acetone/methanol solution of cellulose acetate (2.5%) and PEG-600 (2.5%). The weight ratio of cellulose acetate to PEG-600 in the coating was 1:1, and the final coating was 13.5 weight percent of the total device weight.

EXAMPLE 11

A blend of 100K molecular weight polyethylene oxide (PEO-100K) and the insoluble drug glipizide (95:5) was prepared and pressed into 500 mg tablets using a Manesty Type-F3 tablet press (Manesty Machines Ltd., Liverpool, England). The tablets were spray-coated with a suspension of sucrose (50/60 mesh) in an acetone solution of cellulose acetate (2.5%) and PEG-600 (2.5%). The weight ratio of cellulose acetate to PEG-600 to sucrose in the coating was 1:1:2. The final coating was 13.7 weight percent of the total device weight.

EXAMPLE 12

The procedure of Example 11 was followed to produce tablets as described therein which were then spray coated with suspension of sucrose (30/40 mesh) in an acetone solution of cellulose acetate (4%) and PEG-600 (1%). The weight ratio of cellulose acetate to PEG-600 to sucrose in the coating was 4:1:5. The final coating was 11.8 weight percent of the total device weight.

EXAMPLE 13

The release rates for the devices described in Examples 1–12 were determined according to the procedures described below.

For those devices which contained doxazosin, the device under study was placed in an individual well of a USP dissolution apparatus which well contained 1000 ml of water as the release medium. The well containing the device was stirred at 100 rpm and aliquots of the release medium were removed over time. The aliquots were assayed for doxazosin by measuring UV absorbance at 246 nm.

For those devices which contained glipizide, the device under study was placed in an individual well of a USP dissolution apparatus which well contained 1000 ml of USP Simulated Intestinal Fluid (SIF) without enzymes as the release medium. The well containing the device was stirred at 100 rpm and aliquots of the release medium were removed over time. The aliquots were assayed for glipizide by measuring UV absorbance at 275 nm.

Employing the above described assay procedures, the devices of Examples 1–12 were assayed for release of the beneficial agent and the data is shown in the Tables described below.

TABLE I

Percent of Doxazosin Released over Time from Devices of Examples 1, 2 and 3

| | Percent Doxazosin Released | | |
|---|---|---|---|
| Time(hrs.) | Device of Example 1 | Device of Example 2 | Device of Example 3 |
| 0 | 0 | 0 | 0 |
| 1.50 | 0 | 0 | 0 |
| 3.17 | 12.6 | 1.3 | 0 |
| 4.0 | 18.4 | 5.3 | 0 |
| 5.0 | 25.8 | 8.9 | 1.2 |
| 5.67 | 30.7 | 11.5 | 2.4 |
| 7.67 | 37.6 | 18.5 | 5.0 |
| 9.83 | 52.2 | 26.9 | 8.8 |
| 11.0 | 54.6 | 29.9 | 10.9 |
| 12.25 | 60.0 | 35.2 | 13.2 |
| 13.10 | 61.6 | 37.6 | 14.2 |
| 22.0 | 76.5 | 57.5 | 29.1 |
| 24.0 | 83.2 | 61.1 | 31.8 |
| 26.0 | 85.7 | 63.6 | 33.0 |

Table I, above, shows the release of doxazosin as percent released over time of the devices of Examples 1, 2 and 3. The data show that the rate of release can be varied as a function of the amount of coating (3) applied to the device. For the devices of Examples 1, 2 and 3, as the amount of coating increased the rate of release decreased.

TABLE II

Percent of Doxazosin Released over Time from Devices of Examples 4, 5 and 5

| | Percent Doxazosin Released | | |
|---|---|---|---|
| Time(hrs.) | Device of Example 4 | Device of Example 5 | Device of Example 6 |
| 0 | 0 | 0 | 0 |
| 1.25 | 0 | — | — |
| 1.33 | — | 7.0 | 23.8 |
| 2.0 | — | 15.9 | 35.9 |
| 2.16 | 3.5 | — | — |
| 3.0 | — | 30.2 | 53.0 |
| 3.1 | 9.3 | — | — |
| 4.0 | — | 43.8 | 68.3 |
| 4.1 | 15.4 | — | — |
| 5.0 | — | 54.3 | 80.4 |
| 5.16 | 22.4 | — | — |
| 6.0 | — | 61.5 | 88.1 |
| 6.1 | 28.8 | — | — |
| 7.0 | — | 67.8 | 92.7 |
| 7.1 | 34.5 | — | — |
| 7.85 | 38.7 | — | — |
| 8.0 | — | 74.0 | 96.6 |
| 10.33 | 52.4 | — | — |
| 11.5 | 57.1 | — | — |

Table II, above, shows the release of doxazosin as percent released over time from the devices of Examples 4, 5 and 6. The data show that the rate of release can be varied as a function of the amount of porosigen and, hence, pores (2) contained in the coating (3). For the devices of Examples 4, 5 and 6, the rate of release increased as the amount of porosigen (i.e., hydroxypropyl cellulose) in the coating was increased.

Table III, below, presents data showing the release rate of doxazosin as percent released over time for the device of Example 7.

TABLE III

Percent of Doxazosin Released over Time from the Device of Example 7

| Time(hrs.) | Percent Doxazosin Released |
|---|---|
| 0 | 0 |
| 0.5 | 2.7 |
| 1.0 | 13.4 |
| 1.5 | 21.0 |
| 2.0 | 28.9 |
| 2.5 | 36.4 |
| 3.0 | 44.2 |
| 3.5 | 51.5 |
| 4.0 | 57.3 |
| 4.5 | 61.8 |
| 5.0 | 66.1 |
| 5.75 | 70.6 |
| 7.17 | 76.5 |
| 23.33 | 90.8 |

TABLE IV

Percent of Doxazosin Released over Time from Devices of Examples 8, 9 and 10

| | Percent Doxazosin Released | | |
|---|---|---|---|
| Time(hrs.) | Device of Example 8 | Device of Example 9 | Device of Example 10 |
| 0 | 0 | 0 | 0 |
| 0.5 | 0 | 0 | 0 |
| 1.0 | 0 | 0 | 10.0 |
| 1.5 | 0 | 0 | 22.4 |
| 2.0 | 0 | 10.9 | 33.0 |
| 2.5 | 0 | 20.4 | 43.4 |
| 3.0 | 1.5 | 29.1 | 49.4 |
| 3.5 | 3.9 | 36.3 | 54.3 |
| 4.0 | 7.8 | 41.5 | 59.5 |
| 4.5 | 11.2 | 45.4 | 62.6 |
| 5.0 | 15.2 | 49.2 | 65.7 |
| 5.75 | 20.6 | 52.6 | 67.6 |
| 7.17 | 27.6 | 58.6 | 72.0 |
| 23.33 | 61.1 | 78.0 | 85.2 |

Table IV, above, shows the release of doxazosin as percent released over time from the devices of Examples 8, 9 and 10. The rate of release of doxazosin increased as the amount of PEG-600 in the coating increased. Examination of the devices of Examples 8, 9 and 10 by scanning electron microscopy after release of doxazosin resulted in the inability to locate any pores in the coating at a 0.1 micron lower limit of detection. Therefore, the doxazosin which had a particle size greater than 0.1 micron exited from these devices in solution. Nonetheless, the devices were capable of releasing doxazosin in a controlled manner over time and, further, the rate of release can be controlled by the amount of PEG 600 in the coating. Of course, the limitation for such devices of Examples 8, 9 and 10 is that the beneficial agent(s) must be either soluble in water or, perhaps, of a very small (less than 0.1 micron) particle size.

TABLE V

Percent of Glipizide Released over Time from Devices of Examples 11 and 12

| | Percent Glipizide Released | |
|---|---|---|
| Time(hrs.) | Device of Example 11 | Device of Example 12 |
| 0 | 0 | 0 |
| 1.0 | 12.7 | 0.7 |
| 2.0 | 26.1 | 5.8 |
| 3.33 | 40.0 | 14.9 |
| 5.0 | 50.3 | 25.6 |
| 6.0 | 56.6 | 32.9 |
| 8.25 | 63.8 | 41.1 |
| 9.67 | 67.4 | 45.2 |
| 21.5 | 76.6 | 58.8 |

Table V, above, shows the release of glipizide, an insoluble drug, as percent released over time from the devices of Examples 11 and 12. Examination of the devices of Examples 11 and 12 by scanning electron microscopy following release of glipizide revealed the presence in the coating of pores larger than 245 microns which had been formed upon dissolution of the particulate sucrose.

EXAMPLE 14

Tablets (500 mg) were prepared from a powder blend consisting of PEO-100K, sodium chloride, and glipizide in the weight ratio 76:20:4, using a Carver press under 2 metric tons for 2 seconds. These tablets were spray-coated with a suspension of sucrose (60/80 mesh) in an acetone solution of cellulose acetate (2.5 wt %) and PEG-600 (2.5 wt %). The final weight ratio of cellulose acetate to PEG-600 to sucrose was 1:1:2. The final coating level was 16 weight percent of the final coated tablet weight. The in vitro release of glipizide from these tablets into 0.004M Tris, pH 8.7, was carried out as described in Example 13 and glipizide was assayed by HPLC using a 3.9 mm×15 cm Novapack $C_{18}$ column (Waters Associates, Milford, Mass.) with a mobile phase consisting of 50 volume percent 0.05M sodium phosphate (pH 7.5) and 50 volume percent methanol. The flow rate was 1.0 ml/min. and detection of glipizide was at 227 nm. The in vitro release kinetic profile, shown in Table VI, below, demonstrates controlled release of glipizide from these tablets.

TABLE VI

Percent of Glipizide Released over Time from the Device of Example 14

| Time(hrs.) | Percent Glipizide Released |
| --- | --- |
| 0 | 0 |
| 0.5 | 15.4 |
| 1.0 | 30.4 |
| 1.5 | 44.8 |
| 2.0 | 55.5 |
| 3.0 | 69.9 |
| 4.0 | 77.3 |
| 5.0 | 81.9 |
| 6.0 | 84.6 |
| 7.0 | 86.6 |
| 8.0 | 87.0 |
| 9.0 | 88.7 |
| 10.0 | 89.3 |
| 11.0 | 89.7 |
| 13.0 | 91.0 |
| 15.0 | 91.6 |

EXAMPLE 15

Bilayer tablets of the current invention are prepared as follows. Polyethylene oxide (250 mg) of average molecular weight 300K (PEO-300K) is lightly compressed in a Carver press using a 13/32 inch standard concave lower punch and a 13/32 inch flat upper punch. Doxazosin mesylate is blended with PEO-100K in a ratio of 2:8, and 250 mg of this blend is poured onto the lightly compressed PEO-300K layer in the Carver press. Using a 13/32 inch standard concave upper punch, the two layers are compressed under 2 metric tons for about 2 seconds. The tablets are spray-coated with a suspension of sucrose (30/40 mesh) in an acetone solution of cellulose acetate (4%) and PEG-600 (1%). The final weight ratio of cellulose acetate to PEG-600 to sucrose is 4:1:5. The final coating comprises 5-25 weight percent of the total coated tablet.

EXAMPLE 16

Spherical beads of the type shown in FIG. 4 are prepared as follows. Doxazosin mesylate and PEO-100K are blended in the ratio 1:9. This blend is mixed with a small amount of water in a Hobart mixer. The wet powder is transferred to a Fuji extruder (Fuji Paudal Co., Tokyo, Japan), and short (1 inch×1/16 inch) strands are formed. The extruded material is transferred to a Fuji spheronizer (Fuji Paudal Co., Tokyo, Japan) which transforms the material into beads of approximate diameter 0.5-1.5 mm. After drying, the beads are spray-coated in a Freund CF-granulator (CF-360; Freund Industrial Co., Tokyo, Japan) with an acetone solution of cellulose acetate and HPC (1:1). Alternatively, the drug/PEO beads are spray-coated with a suspension of sucrose (preferably 100/200 mesh) in an acetone solution of cellulose acetate and PEG-600. The final weight ratio of cellulose acetate to PEG-600 to sucrose is 4:1:5; the final coating comprises 5-25 weight percent of the coated bead. An amount of coated beads corresponding to the desired drug dose is filled into a gelatin capsule.

EXAMPLE 17

Spherical multilayered beads of the type shown in FIG. 5 are prepared as follows. PEO-300K is mixed with a small amount of water in a Hobart mixer. The wet powder is transferred to a Fuji extruder, and short (1 inch×1/16 inch) strands are formed. The extruded material is transferred to a Fuji spheronizer which transforms the material into beads of approximate diameter 0.5 mm, which are subsequently dried. Doxazosin mesylate and PEO-100K are blended in the ratio 2.8 and are dissolved in 1:1 methylene chloride/methanol. The PEO-300K beads are coated with the doxazosin mesylate/PEO-100K solution in a Freund CF-granulator. These beads are extensively dried to remove solvents, and then are coated in a Freund CF-granulator with an acetone solution of cellulose acetate and HPC (1:1). Alternatively, the drug/PEO beads are spray-coated with a suspension of sucrose (preferably 100/200 mesh) in an acetone solution of cellulose acetate and PEG-600. The final weight ratio of cellulose acetate to PEG-600 to sucrose is 4:1:5; the final coating comprises 5-25 weight percent of the coated bead. An amount of coated beads corresponding to the desired drug dose is filled into a gelatin capsule.

EXAMPLE 18

Tablets providing a once daily sustained release dose of a decongestant and an antihistamine are prepared as follows. Polyethylene oxide of average molecular weight 100,000 (PEO-100K) is blended with phenylpropanolamine hydrochloride and chlorpheniramine maleate in the ratio 413:75:12. This blend is compressed to form 500 mg tablets using a tablet press. Compressed tablets are spray-coated with a suspension of sucrose (30/40 mesh) in an acetone-solution of cellulose acetate (4%) and PEG-600 (1%). The final weight ratio of cellulose acetate to PEG-600 to sucrose is 4:1:5. The final coating level is 7-25 weight percent of the final coated tablet weight. The release kinetics of the two drugs are assessed using methodology well known in the art, as exemplified in Example 13. These kinetics are used to optimize the rate and duration of drug release by further formulation changes, for example, changes in the PEO molecular weight, the coating level, the coating composition, and by the addition of tablet excipients and/or osmotically effective solutes as will be obvious to those experienced in the art based on the disclosure herein.

EXAMPLE 19

Tablets providing a sustained release dose of an α-blocker/antihypertensive agent and a diuretic/antihypertensive agent are prepared as follows: polyethylene oxide of average molecular weight 100,000 (PEO-100K) is blended with prazosin hydrochloride and polythiazide in the ratio 476:20:4. This blend is compressed to form 500 mg tablets using a tablet press. Compressed tablets are spray-coated with a suspension of sucrose (30/40 mesh) in an acetone solution of cellulose acetate (4%) and PEG-600

(1%). The final coating level is 7–25 weight percent of the final coated tablet weight. The release kinetics of the two drugs are assessed using methodology well known in the art, as exemplified in Example 13. These kinetics are used to optimize the rate and duration of drug release by further formulation changes, for example, changes in the PEO molecular weight, the coating level, the coating composition, and by the addition of tablet excipients and/or osmotically effective solutes, as will be obvious to those experienced in the art based on the current disclosure.

EXAMPLE 20

Bilayer tablets providing a once daily sustained release dose of a decongestant and an antihistamine are prepared as follows. PEO-100K is blended with phenylpropanolamine hydrochloride and chlorpheniramine maleate in the ratio 76:150:24. A bilayer tablet is formed with one layer comprising 250 mg of the PEO-100K/drug blend, and the other layer comprising 250 mg PEO-300K, using a Carver press as described in Example 15. Compressed bilayer tablets are spray-coated with a suspension of sucrose (30/40 mesh) in an acetone solution of cellulose acetate (4%) and PEG-600 (1%). The final weight ratio of cellulose acetate to PEG-600 to sucrose is 4:1:5. The final coating level is 7–25 weight percent of the final coated tablet weight. The release kinetics of the two drugs are assessed using methodology well known in the art, as exemplified in Example 13. These kinetics are used to optimize the rate and duration of drug release by further formulation changes, for example, change in the PEO molecular weight, the coating level, the coating composition, and by the addition of tablet excipients and/or osmotically effective solutes as known in the art and described herein.

What is claimed is:

1. A tablet for releasing a drug to an external environment which comprises:

(a) an innermost hydrogel layer, said innermost hydrogel layer not including drug;

(b) a second layer, said second layer surrounding said innermost layer and said second layer comprising a mixture comprising one or more drugs and from about 50 to about 95 weight percent hydrogel, said hydrogel in said second layer being different from said hydrogel in said first layer; and (c) a coating which surrounds the mixture and which comprises a polymer and one or more porosigens wherein the rate of drug release is relatively independent of the solubility of the drug.

2. The tablet according to claim 1 wherein the hydrogel is polyethylene oxide.

3. The tablet according to claim 2 wherein the coating polymer is cellulose acetate.

4. The tablet according to claim 3 wherein the porosigen is one or more water soluble polymers.

5. The tablet according to claim 4 wherein the water soluble polymer is selected from the group consisting of hydroxypropyl cellulose, polyethylene glycol and polyethylene oxide.

6. The tablet according to claim 3 wherein the porosigens are one or more water soluble polymers and one or more inorganic salts.

7. The tablet according to claim 3 wherein the porosigens are one or more water soluble polymers and one or more water soluble particulate organic compounds and the salts thereof.

8. The tablet according to claim 7 wherein the water soluble polymer is polyethylene glycol-600 and the water soluble particulate organic compound is sucrose.

9. The tablet according to claim 3 wherein the porosigen is one or more inorganic salts or one or more water soluble particulate organic compounds and salts thereof.

10. The tablet according to claim 1 wherein the mixture additionally comprises an osmotically effective solute.

11. The tablet according to claim 1 wherein the coating additionally contains at least one hole.

12. A tablet for releasing a drug to an external environment which comprises:

(a) a first layer comprising a mixture of one or more beneficial agents and from about 50 to about 95 weight percent hydrogel;

(b) a second layer comprising hydrogel which second layer is adjacent to the first layer and comprises an area in contact with the first layer said second layer not including drug, said hydrogel in said second layer being different from said hydrogel in said first layer; and (c) a coating which comprises a polymer and one or more porosigens and which coating surrounds the first and second layers except for said area in contact wherein the rate of drug release is relatively independent of the solubility of the drug.

13. The tablet according to claim 12 wherein the first layer additionally comprises an osmotically effective solute.

14. The tablet according to claim 12 wherein the second layer additionally comprises an osmotically effective solute.

15. The tablet according to claim 12 wherein the first and second layers each additionally comprise an osmotically effective solute.

16. A method for the controlled delivery of one or more beneficial agents to an environment of use which comprises placing the tablet of claim 1 into the environment of use.

17. A method for the controlled delivery of a drug to an animal which comprises administering to the animal the tablet according to claim 1 wherein the beneficial agent is a drug.

* * * * *